United States Patent [19]

Trager et al.

[11] Patent Number: 4,818,513
[45] Date of Patent: Apr. 4, 1989

[54] SEPARATION OF HYDROGEN FLUORIDE FROM 1,1-DIFLUOROETHENE

[75] Inventors: Fred C. Trager, Barberton; J. Douglas Mansell, Akron; W. Eugene Wimer, Uniontown, all of Ohio

[73] Assignee: PPG Industries, Inc., Pittsburgh, Pa.

[21] Appl. No.: 136,217

[22] Filed: Dec. 21, 1987

[51] Int. Cl.⁴ .................. C01B 7/19; C07C 17/34; C07C 19/08; C07C 21/18
[52] U.S. Cl. .................. 423/488; 570/155; 570/156; 570/157; 570/158; 570/136
[58] Field of Search ............... 423/488; 570/155, 156, 570/157, 158, 136

[56] References Cited

U.S. PATENT DOCUMENTS

| | | | |
|---|---|---|---|
| 2,468,681 | 4/1949 | McBride | 423/488 |
| 2,478,933 | 8/1949 | Bratton et al. | 570/156 |
| 2,480,560 | 8/1949 | Downing et al. | 570/149 |
| 2,551,573 | 5/1951 | Downing et al. | 570/134 |
| 2,558,011 | 6/1951 | Sprauser | 423/488 |
| 2,627,529 | 2/1953 | Feasley et al. | 570/155 |
| 2,628,989 | 2/1953 | Miller | 570/156 |
| 2,637,747 | 5/1953 | McBee | 570/167 |
| 2,674,632 | 4/1954 | Skiles | 570/156 |
| 2,687,440 | 8/1954 | McGrew et al. | 570/156 |
| 2,722,558 | 11/1955 | Johnston | 570/153 |
| 2,733,278 | 1/1956 | Anderson | 570/136 |
| 2,734,090 | 2/1956 | Calfee et al. | 570/156 |
| 2,744,148 | 5/1956 | Ruh et al. | 570/168 |
| 2,754,336 | 7/1956 | Chernosky | 570/158 |
| 2,774,798 | 12/1956 | Davis et al. | 570/159 |
| 2,774,799 | 12/1956 | Mantell et al. | 570/156 |
| 2,889,378 | 6/1959 | Boettger et al. | 570/177 |
| 2,909,571 | 10/1959 | Landrum et al. | 570/156 |
| 2,917,556 | 12/1959 | Percival | 570/186 |
| 3,047,637 | 7/1962 | Olstowski | 570/159 |
| 3,073,870 | 1/1963 | Marquis | 570/159 |
| 3,089,910 | 5/1963 | Olstowski et al. | 570/159 |
| 3,118,005 | 1/1964 | Pavlath et al. | 570/156 |
| 3,188,356 | 6/1965 | Hauptschein et al. | 570/155 |
| 3,246,041 | 4/1966 | Miville et al. | 570/155 |
| 3,258,500 | 6/1966 | Swamer et al. | 570/169 |
| 3,428,695 | 2/1969 | Soulen et al. | 570/159 |
| 3,432,562 | 3/1969 | Gardner | 570/156 |

(List continued on next page.)

FOREIGN PATENT DOCUMENTS

| | | |
|---|---|---|
| 704720 | 3/1965 | Canada . |
| 0234002 | 9/1987 | European Pat. Off. ............ 570/156 |
| 1330146 | 5/1963 | France . |
| 1369786 | 7/1964 | France . |
| 395320 | 1/1974 | U.S.S.R. .................. 423/488 |
| 505617 | 7/1976 | U.S.S.R. .................. 570/156 |
| 975498 | 11/1964 | United Kingdom . |
| 1006456 | 10/1965 | United Kingdom . |

OTHER PUBLICATIONS

J. F. Froning et al., *Industrial and Engineering Chemistry*, Mar., 1947, pp. 275–278.
J. H. Simons, *Fluorine Chemistry*, vol. I, Academic Press Inc., New York, 1950, pp. 236–239 and 310–311.
*Chemical Abstracts*, vol. 62, 444e, 1965, Abstracting Fr 1,369,786.
Derwent Abstract of JP 54[1979]-130507 (1979).
F. H. Walker et al., *Journal of Organic Chemistry*, vol. 30 (Oct. 1965), pp. 3284–3285.

*Primary Examiner*—Robert L. Stoll
*Assistant Examiner*—Adriana L. Mui
*Attorney, Agent, or Firm*—George D. Morris

[57] ABSTRACT

A gaseous feed stream comprising hydrogen fluoride and 1,1-difluoroethane is contacted with liquid organic barrier material in a condensing zone to partially condense the feed stream. The gaseous phase remaining after the partial condensation comprises most of the 1,1-difluoroethane originally present in the feed stream while the liquid condensate comprises most of the hydrogen fluoride originally present in the feed stream. The gaseous phase and the liquid condensate are removed from the condensing zone as separate streams. Less than about 50 percent of the 1,1-difluoroethane originally present in the feed stream reacts with hydrogen fluoride to form 1,1,1-trifluoroethane during the partial condensation and the removal of the separate streams from the condensing zone. The preferred liquid organic barrier material is 1,1,-trifluoroethane.

14 Claims, 2 Drawing Sheets

OTHER PUBLICATIONS

| | | | |
|---|---|---|---|
| 3,442,961 | 5/1969 | Hutton | 570/180 |
| 3,444,251 | 5/1969 | Gardner | 570/156 |
| 3,456,025 | 7/1969 | Gardner | 570/156 |
| 3,557,228 | 1/1971 | Moyer et al. | 570/225 |
| 3,600,450 | 8/1971 | Kaess et al. | 570/156 |
| 3,636,172 | 1/1972 | Gardner | 570/157 |
| 3,723,549 | 3/1973 | Kaess et al. | 570/160 |
| 3,755,477 | 8/1973 | Firth et al. | 570/165 |
| 3,830,856 | 8/1974 | Muessdoerffer | 570/155 |
| 3,833,675 | 9/1974 | Ukaji et al. | 570/246 |
| 3,862,995 | 1/1975 | Martens et al. | 570/168 |
| 3,996,299 | 12/1976 | Fozzard | 570/132 |
| 3,996,301 | 12/1976 | Fozzard | 570/153 |
| 4,053,529 | 10/1977 | Martens | 570/155 |
| 4,086,407 | 4/1978 | Fozzard | 526/75 |
| 4,087,475 | 5/1978 | Jordan | 570/142 |
| 4,147,733 | 4/1979 | Fiske et al. | 570/160 |
| 4,148,831 | 4/1979 | Schultz et al. | 570/155 |
| 4,178,316 | 12/1979 | Schultz et al. | 570/154 |
| 4,613,709 | 9/1986 | Franklin | 570/227 |

SEPARATION OF HYDROGEN FLUORIDE FROM 1,1-DIFLUOROETHENE

BACKGROUND OF THE INVENTION

The pyrolysis of 1,1,1-trifluoroethane (viz., methylfluoroform) at elevated temperatures (about 400° C. to about 1500° C.) to form 1,1-difluoroethene (viz., vinylidene fluoride) and hydrogen fluoride is known; see U.S. Pat. Nos. 2,480,560; 3,188,356; and 3,456,025, the disclosures of which are, in their entireties, incorporated herein by reference. The reaction is reversible and may be represented by the equation

$$CH_3CF_3 \rightleftarrows CH_2=CF_2 + HF$$

At the elevated temperatures of the pyrolysis, the gas-phase reaction proceeds readily to the right, while in the liquid phase the reaction proceeds rapidly to the left.

Two experiments were conducted which illustrate the rapidity of the reverse reaction in the liquid phase. Individual sources of nitrogen, hydrogen fluoride, and 1,1-difluoroethene were connected through valves, tees and rotameters to the entrance tube of a reaction vessel. The reaction vessel was a Kel-F ® polymer test tube having a length of 15.24 centimeters and a diameter of 3.81 centimeters equipped with a neoprene two-hole stopper and containing a magnetic stirring bar. The entrance tube passed through one hole of the stopper and was equipped with a polyethylene frit for dispersal of the introduced gas. Sufficient clearance was allowed between the frit and the bottom of the reactor for the magnetic stirring bar to spin. An exit tube passed through the second hole of the stopper and permitted gas to be removed from the upper portion of the reaction vessel. The exit tube was sequentially connected to a water scrubber, a drying tube containing potassium hydroxide pellets, and an exit rotameter. Gas samples were taken through rubber tubing connected to the outlet of the exit rotameter. The rotameter for measuring the introduced 1,1-difluoroethene and the exit rotameter were identical rotameters. This permitted a comparison of the 1,1-difluoroethene entrance flow rate and the exit gas flow rate during the experiments. The reaction vessel was immersed in a cooling bath positioned over a magnetic stirrer drive unit. For the experiment conducted at 0° C., wet ice was used as the cooling bath. For the experiment conducted at −25° C., a solid carbon dioxide and carbon tetrachloride bath was used. At the start of each experiment, nitrogen was passed through the system and the reaction vessel was cooled to the desired temperature. The flow of nitrogen was discontinued and hydrogen fluoride was condensed to provide 75 milliliters of liquid in the reaction vessel. The flow of hydrogen fluoride was then discontinued and 1,1-difluoroethene was bubbled at a flow rate of 40 milliliters (referenced to 25° C. and ambient atmospheric pressure) per minute into the liquid hydrogen fluoride. In both cases there was substantial absorption of 1,1-difluoroethene in the hydrogen fluoride during approximately the first five minutes of flow. Thereafter, the entrance and exit flow rates were identical. Gas-liquid chromatographic analyses of samples of the exit gas taken after establishment of identical flow rates showed that 95 percent of the introduced 1,1-difluoroethene reacted with hydrogen fluoride at 0° C. to form 1,1,1-trifluoroethane, while 96 percent of the introduced 1,1-difluoroethene reacted with hydrogen fluoride at −25° C. to form 1,1,1-trifluoroethane.

Because of the rapidity of the reverse reaction at low 1,1-difluoroethene, it was long believed that partial condensation of the reaction products of the pyrolysis reaction to achieve the recovery of 1,1-difluoroethene which is essentially free of hydrogen fluoride would not be practical in a commercial process. The prior art processes, therefore, sought to quickly convert the hydrogen fluoride to a form which would be essentially unreactive with 1,1-difluoroethene by the time low temperatures favoring reversion were reached.

In Examples I and II of the U.S. Pat. No. 2,480,560 the pyrolysis reaction products were washed with water, presumably in a quenching operation. The ultimate yields of 1,1-difluoroethene are not given, but in any event the hydrogen fluoride would be absorbed by the water to form aqueous hydrofluoric acid. Substantially anhydrous hydrogen fluoride can be obtained from aqueous hydrofluoric acid, but because of the high affinity of hydrogen fluoride for water, the dehydration processes are energy intensive and both capital expenditures and operating costs are high.

U.S. Pat. No. 3,456,025 discloses the removal of hydrogen fluoride with water or an aqueous solution of caustic; in the Example aqueous caustic was used. The reaction of hydrogen fluoride with aqueous caustic produces sodium fluoride from which hydrogen fluoride can be obtained by acidification with a mineral acid such as sulfuric acid. This regeneration process requires water removal at some point in the process. It is also ultimately energy intensive, expensive from the standpoints of capital expenditures and operating costs, and produces a by-product such as sodium sulfate that must be used in some fashion or properly disposed.

In the Examples of U.S. Pat. No. 3,188,356, the pyrolysis reaction products were passed through a tube packed with sodium fluoride heated to 100° C. to remove hydrogen fluoride. Judging from J. F. Froning et al, "Purification and Compression of Fluorine", *Industrial and Engineering Chemistry*, March 1947, pages 275–278, and J. H. Simons, *Fluorine Chemistry*, Vol. I, Academic Press, Inc., New York, 1950, pages 310–311, both of which deal with the removal of hydrogen fluoride from elemental fluorine, the removal of hydrogen fluoride according to U.S. Pat. No. 3,188,356 would be accomplished through formation of the sodium fluoride-hydrogen fluoride complex, NaF.HF. Both of these documents present a table of equilibrium pressures of hydrogen fluoride over a mixture of NaF and NaF.HF at various temperatures and the Froning et al paper discusses operating an absorption tower containing sodium fluoride to alternately absorb hydrogen fluoride from elemental fluorine and then to regenerate hydrogen fluoride. It would accordingly be expected that such a cyclic absorption-regeneration technique would be effective in removing hydrogen fluoride from the pyrolysis products of U.S. Pat. No. 3,188,356 and in providing substantially anhydrous hydrogen fluoride. In order to incorporate such cyclic absorption-regeneration techniques into a continuous system, however, a plurality of units operating at differing phases in the cycle must be employed. The capital expenditures are therefore high. Inasmuch as the absorption bed must be heated and cooled in cyclic fashion, the energy requirements and operating expenses are high. It is more efficient to avoid the incorporation of cyclically functioning units in an overall continuous process when this is possible.

THE INVENTION

It has now been discovered that partial condensation can be used to achieve an efficient separation of hydrogen fluoride from gaseous mixtures comprising hydrogen fluoride and 1,1-difluoroethene without incurring a large reversion of these compounds, if a liquid organic barrier material is properly employed during the partial condensation. Accordingly, one embodiment of the invention is a process comprising: (a) introducing a gaseous feed stream comprising hydrogen fluoride and 1,1-difluoroethene to a condensing zone, (b) contacting the feed stream in the condensing zone with liquid organic barrier material to partially condense the feed stream and produce a gaseous phase comprising most of the 1,1-difluoroethene originally present in the feed stream and a liquid condensate comprising most of the hydrogen fluoride originally present in the feed stream, and (c) removing the gaseous phase and the liquid condensate from the condensing zone as separate streams, wherein less than about 50 percent of the 1,1-difluoroethene originally present in the feed stream reacts with hydrogen fluoride to form 1,1,1-trifluoroethane during the partial condensation and the removal of the separate streams from the condensing zone.

In many cases less than about 25 percent of the 1,1-difluoroethene originally present in the feed stream reacts with hydrogen fluoride to form 1,1,1-trifluoroethane during the partial condensation and the removal of the separate streams from the condensing zone. Often less than about 10 percent of the 1,1-difluoroethene originally present in the feed stream reacts with hydrogen fluoride to form 1,1,1-trifluoroethane during the partial condensation and the removal of the separate streams from the condensing zone. Preferably, less than about 5 percent of the 1,1-difluoroethene originally present in the feed stream reacts with hydrogen fluoride to form 1,1,1-trifluoroethane during the partial condensation and the removal of the separate streams from the condensing zone.

The feed stream may consist essentially of hydrogen fluoride and 1,1-difluoroethene, but usually the feed stream comprises one or more other compounds in addition to hydrogen fluoride and 1,1-difluoroethene.

The concentrations of hydrogen fluoride and 1,1-difluoroethene originally present in the feed stream may vary widely. In most cases, however, the feed stream comprises at least about 20 mole percent hydrogen fluoride and about 20 mole percent 1,1-difluoroethene. Often the feed stream comprises at least about 30 mole percent hydrogen fluoride and at least about 30 mole percent 1,1-difluoroethene. Frequently the feed stream comprises from about 20 to about 50 mole percent hydrogen fluoride and from about 20 to about 50 mole percent 1,1-difluoroethene. In many cases the feed stream comprises from about 20 to about 40 mole percent hydrogen fluoride and from about 20 to about 40 mole percent 1,1-difluoroethene.

The gaseous phase which is removed from the condensing zone comprises most of the 1,1-difluoroethene originally present in the feed stream to the condensing zone. Usually the gaseous phase which is removed comprises at least about 50 percent of the 1,1-difluoroethene originally present in the feed stream. Often the gaseous phase which is removed comprises at least about 75 percent of the 1,1-difluoroethene originally present in the feed stream. In many cases the gaseous phase which is removed comprises at least about 90 percent of the 1,1-difluoroethene originally present in the feed stream. It is preferred that the gaseous phase which is removed comprise at least about 95 percent of the 1,1-difluoroethene originally present in the feed stream.

The gaseous phase which is removed from the condensing zone usually comprises less than about 10 percent of the hydrogen fluoride originally present in the feed stream to the condensing zone. In many cases the gaseous phase which is removed from the condensing zone comprises less than about 5 percent of the hydrogen fluoride originally present in the feed stream. Preferably, the gaseous phase which is removed from the condensing zone comprises less than about 2 percent of the hydrogen fluoride originally present in the feed stream.

The liquid condensate which is removed from the condensing zone comprises most of the hydrogen fluoride originally present in the feed stream to the condensing zone. In many cases the liquid condensate which is removed from the condensing zone comprises at least about 40 percent of the hydrogen fluoride originally present in the feed stream. Frequently the liquid condensate which is removed from the condensing zone comprises at least about 65 percent of the hydrogen fluoride originally present in the feed stream. It is preferred that the liquid condensate which is removed from the condensing zone comprise at least about 90 percent of the hydrogen fluoride originally present in the feed stream.

The liquid condensate which is removed from the condensing zone usually comprises less than about 2 percent of the 1,1-difluoroethene originally present in the feed stream to the condensing zone. In many cases the liquid condensate which is removed from the condensing zone comprises less than about 1 percent of the 1,1-difluoroethene originally present in the feed stream to the condensing zone. Often the liquid condensate which is removed the from the condensing zone comprises less than about 0.1 percent of the 1,1-difluoroethene originally present in the feed stream. Preferably it comprises less than about 0.1 percent of the 1,1-difluoroethene originally present in the feed stream.

When the feed stream comprises one or more compounds in addition to hydrogen fluoride and 1,1-difluoroethene, they or their reaction products will be found in the gaseous phase removed from the condensing zone, the liquid condensate removed from the condensing zone, or both. Examples of such compounds as might be present include 1,1,1-trifluoroethane, 1-chloro-1,1,-difluoroethane, nitrogen, carbon dioxide, and water.

The liquid organic barrier material comprises an organic compound or mixture of such compounds which is essentially inert during the partial condensation and which has a boiling point at the pressure prevailing in the condensing zone, intermediate between the boiling points of hydrogen fluoride and 1,1-difluoroethene under the same conditions of pressure. In most cases the boiling point of the liquid organic barrier material is at least about 10 Celsius degrees below that of hydrogen fluoride and at least about 10 Celsius degrees above that of 1,1-difluoroethene. Preferably the boiling point of the liquid organic barrier material is at least about 50 Celsius degrees below that of hydrogen fluoride and at least about 30 Celsius degrees above that of 1,1-difluoroethene.

Examples of compounds which may be employed as the liquid organic barrier materials include 1,1,1-trifluoroethane, difluoromethane, chlorodifluoromethane, dichlorodifluoromethane, propane, normal butane, and isobutane. Compounds containing only carbon, hydrogen, and fluorine are preferred for use as barrier materials. Of these, 1,1,1-trifluoroethane is especially preferred. Under the conditions of use it is rare that the liquid organic barrier material will contain only one compound. After running the process for a while, some other compounds may also be found to be present, usually in small amounts when compared with the principal compound. When the feed stream is of essentially constant composition, the concentrations of these other compounds generally reach at least approximately steady states. It is particularly preferred that the liquid organic barrier material be rich in 1,1,1-trifluoroethane.

The pressure at which the partial condensation may be conducted may vary widely. It may be subatmospheric, ambient atmospheric, or superatmospheric. In most cases it is at about ambient atmospheric or a little higher. In many cases the pressure is in the range of from about −35 to about 690 kilopascals, gauge. Preferably the pressure is in the range of from about 0 to about 345 kilopascals, gauge.

It is well known that liquid mixtures of hydrogen fluoride and most fluorocarbons form two liquid phases at pressures at or near ambient atmospheric pressure. In some cases by the imposition of substantial superatmospheric pressure, the temperatures at which liquid can exist can be high enough so that only one liquid phase is present. Therefore, in one embodiment of the invention, the liquid condensate formed during the partial condensation consists essentially of one phase which comprises liquid organic barrier material and most of the hydrogen fluoride originally present in the feed stream. These components can be substantially separated by distillation when desired.

In the preferred embodiment of the invention, however, the liquid condensate formed during the partial condensation comprises two liquid phases, one of the liquid phases comprising most of the hydrogen fluoride originally present in the feed stream and the other liquid phase being rich in liquid organic barrier material.

The liquid phases may be removed from the condensing zone as separate streams, but it is preferred to remove them as a single stream in order to minimize the exposure of liquid hydrogen fluoride to 1,1-difluoroethene.

A multiphase condensate is particularly advantageous because of the flexibility with which it may be dealt.

In one embodiment, the liquid phases of the multiphase condensate are separated into separate streams by conventional techniques such as decantation, withdrawal of the lower phase, or centrifugation. The liquid phase which is rich in liquid organic barrier material may be recycled in whole or in part to the condensing zone or it may be used for other purposes. For example, when this liquid phase is rich in 1,1,1,-trifluoroethane, it may be recycled to a pyrolysis reactor for producing additional 1,1-difluoroethene and hydrogen fluoride. The liquid phase which comprises most of the hydrogen fluoride originally present in the feed stream is ordinarily substantially anhydrous and may be used as a source of hydrogen fluoride for various purposes, especially hydrofluorination reactions. It is useful, for example, as a portion of the hydrogen fluoride feed stock to a reaction in which hydrogen fluoride is reacted with 1,1-dichloroethene to form 1,1,1-trifluoroethane and hydrogen chloride. See U.S. Pat. Nos. 2,637,747; 3,755,477; and 4,147,733; the disclosures of which are, in their entireties, incorporated herein by reference.

Although some liquid organic barrier materials, such as for example 1,1,1-trifluoroethane, are for all practical purposes substantially immiscible with liquid hydrogen fluoride at about ambient pressure, their densities are relatively close to that of liquid hydrogen fluoride. Nevertheless, the difference in densities is sufficient so that satisfactory phase separation may be achieved in a phase separator if the mixture is allowed to stand more or less quiescently over a rather prolonged period of time which will vary depending upon such factors as the identities and concentrations of impurities in the phases, temperature, and the degree of quiescence maintained. Centrifugation can be used to accelerate the separation, but the cost of centrifuges is high.

Although the difference in densities of some liquid organic barrier materials and liquid hydrogen fluoride may be small, the difference in boiling points is often wide. The difference in the boiling points of liquid 1,1,1-trifluoroethane and liquid hydrogen fluoride, for example, amounts to about 65 Celsius degrees at ambient atmospheric pressure. A conventional distillation column having the separating capacity of at least one or a few plates may therefore be used in lieu of a phase separator for separation of the two liquid phases.

The partial condensation process of the present invention is especially advantageous when combined with a process in which 1,1,1-trifluoroethane is pyrolyzed to form 1,1-difluoroethene and hydrogen fluoride. Inasmuch as the conversion of 1,1,1-trifluoroethane is usually in the range of from about 20 percent to about 80 percent, the 1,1,1-trifluoroethane in the effluent from the pyrolysis reactor is, upon partial condensation of the effluent, useful as a source of liquid organic barrier material for the partial condensation of subsequently fed effluent from the pyrolysis reactor.

BRIEF DESCRIPTION OF THE DRAWINGS

For a better understanding of the intention, reference may be made to the drawings wherein like numerals refer to like parts in which.

DETAILED DESCRIPTION OF THE DRAWING

Figure 1:
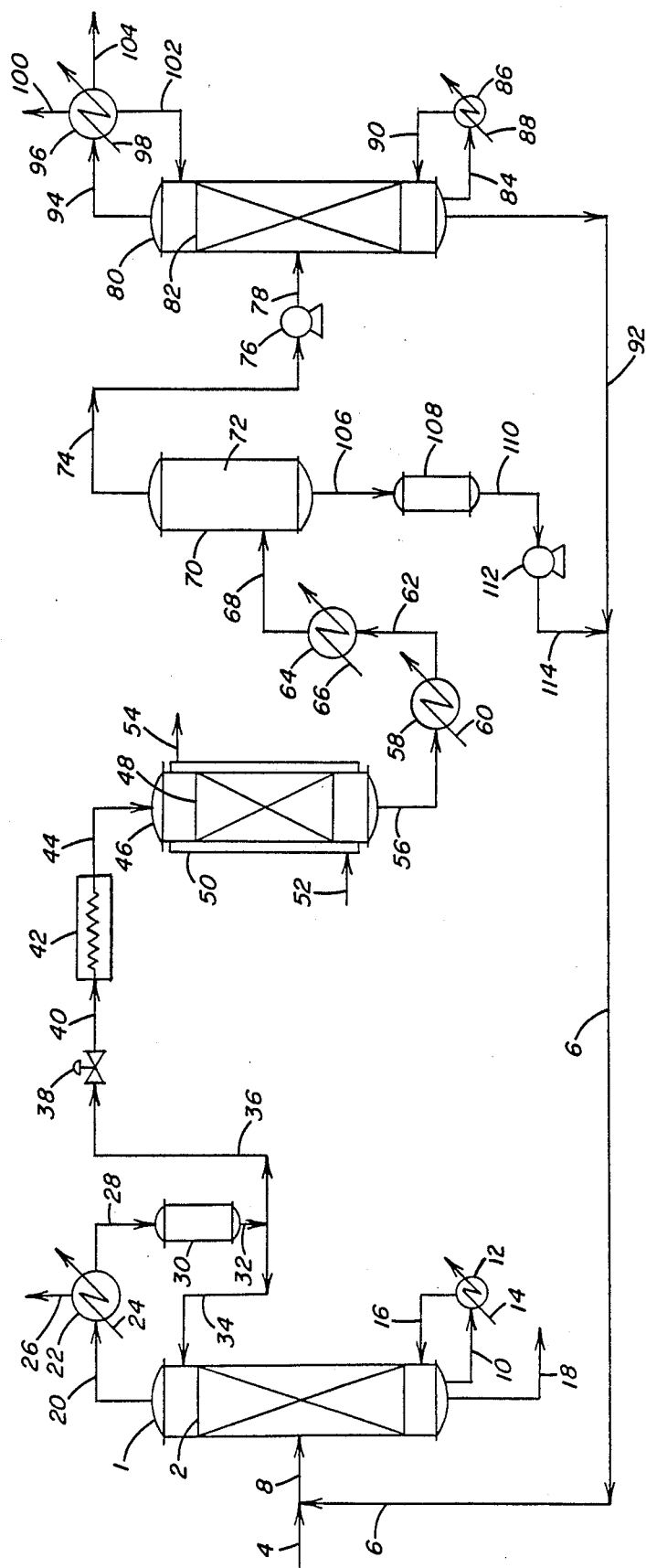
FIG. 1 shows diagrammatically an embodiment of the invention.

Referring now in detail to the drawings, there is shown diagrammatically in FIG. 1 a distillation column 1 which contains packing 2. Liquid 1,1,1-trifluoroethane from line 4 is admixed with liquid 1,1,1-trifluoroethane and liquid hydrogen fluoride from line 6 and the mixture passed through line 8 into distillation column 1. The 1,1,1-trifluoroethane passing through line 4 may be from any source. It may be essentially pure or it may contain minor contaminating amounts of impurities depending upon the source of the material. Examples of such impurities include hydrogen fluoride and various organic compounds which, in addition to carbon, contain hydrogen, chlorine, and/or fluorine atoms. A preferred source of the material passing through line 4 is a reaction in which hydrogen fluoride is reacted with 1,1-dichloroethene to form 1,1,1,-trifluoroethane and hydrogen chloride, and from which essentially all of the hydrogen chloride has been removed by distillation. Distillation column 1 operates at about 1380 kilopascals, gauge. Bottoms liquid is passed through line 10 to reboiler 12 heated by steam or other hot heat transfer fluid introduced to line 14. In reboiler 12 the bottoms liquid is boiled, thereby producing vapor which returns to distillation column 1 through line 16. A portion of the bottoms liquid, which is essentially substantially anhydrous hydrogen fluoride containing most of the impurities, if any, present in the material introduced through line 4, is removed through line 18 for such use as may be desired. It is preferred that the material passing through line 18 be passed as recycle to a reaction in which hydrogen fluoride is reacted with 1,1-dichloroethene to form 1,1,1-trifluoroethane and hydrogen chloride. A stream of gaseous overhead, which compromises 1,1,1-trifluoroethane as the principal constituent, is removed from distillation column 1 through line 20 and forwarded to condenser 22 cooled by coolant passing through line 24. In condenser 22 most of the gas is condensed to a liquid. Uncondensed gases may be removed through line 26. Liquid condensate is removed from condenser 22 through line 28 and forwarded to tank 30 which serves as a hold-up vessel. Liquid is removed from tank 30 through line 32 and split into two streams passing through lines 34 and 36, respectively. The stream passing through line 34 is returned to distillation column 1, as reflux. The stream passing through line 36 is passed through control valve 38 and line 40 to preheater 42 which may be heated by any convenient means. In passing through control valve 38, the pressure of the stream is reduced to about 70 kilopascals, gauge. Preheater 42 serves to vaporize liquid present, if any, in the stream flowing through line 40 and to preheat the vapor to about −10° C. Vapor from preheater 42 is introduced through line 44 to the top of pyrolysis reactor 46 containing a porous bed 48 initially of particulate alumina which is supported by a perforated plate, not shown. Jacket 50 is affixed to most of the periphery of reactor 46. Hot heat transfer fluid is introduced to jacket 50 through line 52 for heating purposes and removed through line 54. The temperature of reactor 46 is maintained at about 525° C. If porous bed 48, which is optional, is omitted, the temperature of reactor 46 is maintained at about 800° C. During its passage through reactor 46, a portion of the 1,1,1-trifluoroethane is pyrolyzed to form 1,1-difluoroethene and hydrogen fluoride. The effluent from reactor 46, which effluent comprises 1,1-difluoroethene, hydrogen fluoride, and 1,1,1-trifluoroethane, is removed through line 56 and introduced to cooling system 58 where the effluent is cooled to about 150° C. by coolant passing through line 60. The cooled gas stream is passed from cooling system 58 through line 62 to cooling system 64 where it is further cooled to about 50° C. by coolant passing through line 66. The stream leaving cooling system 64 is still gaseous and is passed through line 68 as a feed stream to partial condenser 70 where it is partially condensed within condensing zone 72 by contact with liquid organic barrier material rich in 1,1,1-trifluoroethane. The operation of partial condenser 70 is discussed in more detail below. A gaseous phase, which comprises most of the 1,1-difluoroethene originally present in the feed stream which passed through line 68 and some of the 1,1,1-trifluoroethane, is removed from partial condenser 70 and condensing zone 72 through line 74 and introduced to compressor 76 where the gas is compressed to about 1380 kilopascals, gauge. The compressed gas is forwarded through line 78 to distillation column 80 which contains packing 82. Bottoms liquid is passed through line 84 to reboiler 86 heated by steam or other hot heat transfer fluid introduced to line 88. In reboiler 86 the bottoms liquid is boiled, thereby producing vapor which returns to distillation column 80 through line 90. A portion of the bottoms liquid, which comprises 1,1,1-trifluoroethane as the principal constituent, is removed through line 92 and forwarded to line 6. A stream of gaseous overhead, which comprises 1,1-difluoroethene as the principal constituent, is removed from distillation column 80 through line 94 and forwarded to condenser 96 cooled by coolant passing through line 98. In condenser 96 most of the gas is condensed to a liquid. Uncondensed gases may be removed through line 100. The liquid condensate removed from condenser 96 is essentially 1,1-difluoroethene. A portion of the liquid condensate is removed from condenser 96 through line 102 and returned to distillation column 80 as reflux. The remainder of the liquid condensate is removed from condenser 96 through line 104 as product. Liquid condensate leaving partial condenser 70 and condensing zone 72 through line 106 comprises two liquid phases. The lighter liquid phase is essentially anhydrous hydrogen fluoride and comprises most of the hydrogen fluoride initially present in the feed stream which passed through line 68. The denser liquid phase comprises 1,1,1-trifluoroethane as the principal constituent. The liquid condensate passing through line 106 is introduced to tank 108 which serves as a hold-up vessel. Liquid is removed from tank 108 through line 110 and introduced to pump 112. Pump 112 increases the pressure to about 1380 kilopascals, gauge, and forwards the liquid through line 114 to line 6.

Figure 2:
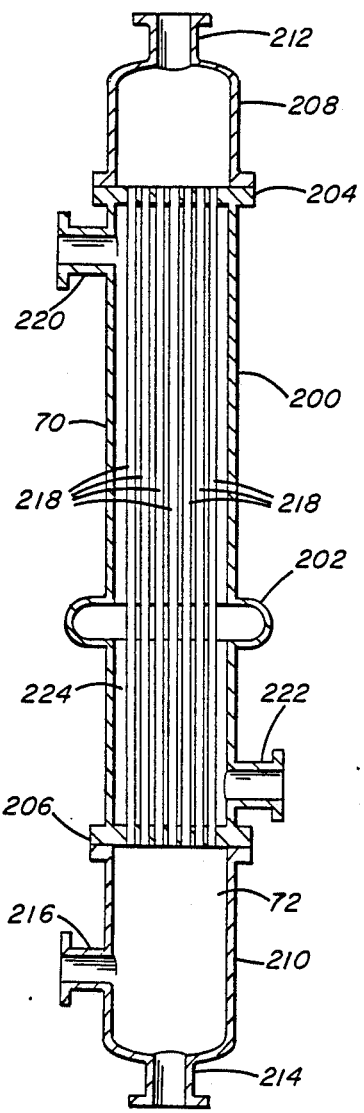
FIG. 2 shows diagrammatically in cross-section an apparatus which may be employed to provide the condensing zone in the invention.

There are many embodiments of partial condenser 70 which may be employed to provide condensing zone 72. One such embodiment is shown diagrammatically in FIG. 2. In this embodiment partial condenser 70 comprises shell 200 containing expansion joint 202. Tubesheet 204 and tubesheet 206 are attached, respectively, to the upper and lower ends of shell 200. Head 208 is attached to tubesheet 204 and head 210 is attached to tubesheet 206. Overhead vapor outlet 212 is attached to the upper end of head 208. Condensate outlet 214 and feed stream inlet 216 are attached to the bottom and side of head 210, respectively. Tubes 218 pass through and are attached at their upper and lower end portions to tubesheet 204 and tubesheet 206, respectively. The interiors of head 208, tubes 218, and head 210 constitute condensing zone 72. Coolant inlet 220 and coolant outlet 222 are attached near the upper and lower ends of shell 200, respectively. Coolant flows within shell-side region 224, that is, the region bounded by the interiors of shell 200 and tubesheets 204 and 206 and by the exteriors of tubes 218. Baffles, not shown, may be positioned at various locations within shell-side region 224 in accordance with conventional condenser practice, when desired.

Although it is not desired to be bound by any theory, it is believed that during essentially steady-state operation, the condensate within tubes 218 is essentially liquid organic barrier material rich in 1,1,1-trifluoroethane and containing little or no liquid hydrogen fluoride. As the cold liquid organic barrier material drops from the interiors of tubes 218 into the interior of head 210 it contacts the feed stream entering through feed stream inlet 216 and condenses most of the hydrogen fluoride originally present in the feed stream. At least some of the liquid organic barrier material and the liquid hydrogen fluoride fall to the bottom of head 210 and leave condensing zone 72 as two liquid phases through condensate outlet 214. Most of the gaseous 1,1-difluoroethene originally present in the feed stream and usually some of the gaseous organic barrier material pass upwardly through tubes 218 into the interior of head 208. The vapor then leaves condensing zone 72 through overhead vapor outlet 212.

Although the theoretical reasons are not well understood, partial condensation in accordance with the invention provides efficient separation of 1,1-difluoroethene and hydrogen fluoride with surprisingly little reversion of 1,1-difluoroethene and hydrogen fluoride to 1,1,1-trifluoroethane.

The process and apparatus shown in FIG. 1 can be varied in many ways.

Figure 3:
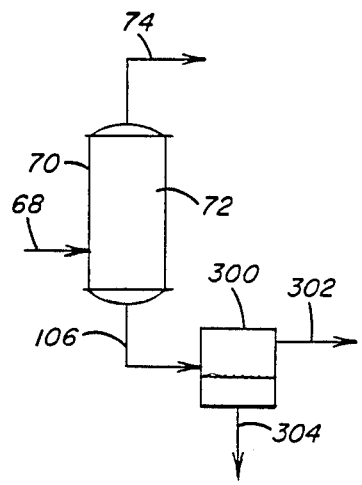
FIG. 3 shows diagrammatically a modification which can be made to the embodiment of FIG. 1.

One such variation is shown diagrammatically in FIG. 3. In this variation the two-phase liquid condensate leaving partial condenser 70 and condensing zone 72 is passed through line 106 to phase separator 300 rather than to tank 108 (FIG. 1). In phase separator 300 the phases separate into an upper liquid layer comprising most of the hydrogen fluoride initially present in the feed stream which passed through line 68 and lower liquid layer comprising 1,1,1-trifluoroethane. The upper layer, which is substantially anhydrous hydrogen fluoride, is removed from phase separator 300 through line 302 for such use as may be desired. The lower liquid layer is removed from phase separator 300 through line 304 and forwarded either to pump 112 (FIG. 1) or to line 40 (FIG. 1).

Although liquid 1,1,1-trifluoroethane and liquid hydrogen fluoride are, for all practical purposes, substantially immiscible, their densities are relatively close together. Nevertheless the difference in densities is sufficient so that satisfactory phase separation may be achieved in phase separator 300 if the mixture is allowed to stand more or less quiescently over a rather prolonged period of time which will vary depending upon factors such as the identities and concentrations of impurities in the phases, the temperature, and the degree of quiescence maintained. Faster phase separation may be achieved through use of a centrifuge in the lieu of phase separator 300 which depends upon the local acceleration of gravity. Although the difference in densities of liquid hydrogen fluoride and liquid 1,1,1-trifluoroethane is small, the difference in boiling points is wide, amounting to about 65 Celsius degrees at ambient atmospheric pressure. A conventional distillation column having the separating capacity of one or a few plates (or more if desired), may therefore be used in lieu of phase separator 300 for separation of the two liquid phases passing through line 106 when it is desired to reduce the time involved in achieving phase separation.

Figure 4:
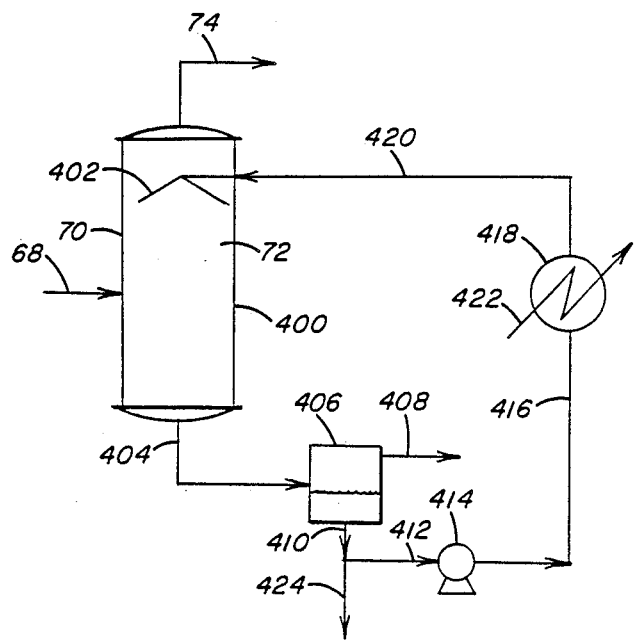
FIG. 4 shows diagrammatically a further modification which can be made to the embodiment of FIG. 1.

Another variation is shown diagrammatically in FIG. 4. Here the structure and operation of partial condenser 70 are different than that shown in FIG. 2. In this embodiment partial condenser 70 comprises shell 400 and spray head 402. Cool liquid organic barrier material which is rich in 1,1,1-trifluoroethane is sprayed from spray head 402 so as to rain down upon the feed stream introduced through line 68. This causes partial condensation of the feed stream in such a manner that the contact time between liquid hydrogen fluoride and gaseous 1,1-difluoroethene is small. The two-phase liquid condensate leaving partial condenser 70 and condensing zone 72 is passed through line 404 to phase separator 406 which functions in essentially the same manner as phase separator 300 (FIG. 3). The upper layer, which is essentially substantially anhydrous hydrogen fluoride, is removed from phase separator 406 through line 408 for such use as may be desired. The lower liquid layer is removed from phase separator 406 through line 410 and split into two streams. One of the streams is introduced through line 412 to pump 414 which circulates the stream through line 416, cooler 418, and line 420 to spray head 402 as a source of the cool liquid barrier material which is sprayed through spray head 402. Cooler 418 is cooled by coolant passing through line 422. The other stream resulting from splitting the material flowing in line 410 into two streams is forwarded through line 424 to either pump 112 (FIG. 1) or line 40 (FIG. 1). As in the case described above, a centrifuge or distillation column may be used in lieu of phase separator 406. When a distillation column is employed, the condenser may be used, if desired, to cool the condensate to the desired temperature for forwarding to spray head 402, thereby eliminating cooler 418 and line 422 from the system.

Referring again to FIG. 1, the purpose of compressor 76 and pump 112 is to permit condensers 22 and 96 to operate at higher temperatures than would be required if distillation columns 1 or 80 and their associated equipment including condensers 22 and 96, were operated at or about ambient atmospheric pressure. Nevertheless, if it is desired to operate condensers 22 and 96 at temperatures sufficiently low to condense the vapor passing through lines 20 and 94, respectively, then compressor 76 and pump 112 may be eliminated from the system. In this case, the pressure drop across control valve 38 will be correspondingly smaller. The same principles are applicable to variations in the process of FIG. 1 such as those described in respect of FIGS. 3 and 4.

For the sake of clarity in setting forth the nature of the invention, parts of the apparatus such as valves, pumps, flow indicators, pressure indicators, pressure reducers, temperature indicators, hold-up tanks, storage tanks, and the like, not essential to a complete understanding of the invention, have been omitted from the drawings.

It will be appreciated that various modifications can be made to the systems of the drawings without departing from the spirit of the invention. For example, the distillation columns may be bubble cap columns, sieve plate columns, or similar devices. Single condensers may be replaced with a plurality of condensers operating in series and/or parallel. So likewise with the coolers. Other modifications will be apparent to those skilled in the art.

The invention is further described in conjunction with the following examples, which are to be considered illustrative rather than limiting, and in which all parts by weight and all percentages are percentages by weight unless either expressly or contextually qualified otherwise.

EXAMPLES

An apparatus for partially condensing gaseous mixtures of 1,1,1-trifluoroethane, 1,1-difluoroethene, and hydrogen fluoride was constructed. Individual cylinders of 1,1,1-trifluoroethane, 1,1-difluoroethene, and hydrogen fluoride were connected through individual valves and flow meters to a manifold where gases were mixed in the above order to provide a gaseous feed stream. The flow meters for 1,1,1-trifluoroethane and 1,1-difluoroethane were glass rotameters; the flow meter for hydrogen fluoride was a MONEL ® alloy body Matheson mass flow meter. The hydrogen fluoride cylinder, the hydrogen fluoride valve, the hydrogen fluoride flow meter, and the tubing carrying hydrogen fluoride to the manifold were wrapped with heavy silicone rubber coated electrical heating tape. A thermocouple was inserted between the heating tape and the hydrogen fluoride cylinder. An autotransformer supplying electrical power to the heating tape was used to maintain a temperature of about 40° C. at the location of the thermocouple; this produced enough hydrogen fluoride pressure for stable metering to the system and assured that 1,1-difluoroethene did not back up into the hydrogen fluoride cylinder. Both the 1,1,1-trifluoroethane cylinder and the 1,1-difluoroethene cylinder were of one-liter capacity. The capacity of the hydrogen fluoride cylinder was 300 milliliters. The outlet from the manifold was connected to the feed stream inlet of a partial condenser which provided the condensing zone, viz., the interior of the partial condenser. The partial condenser was fabricated from MONEL ® alloy and stainless steel, and contained a condensing coil and a condensate deflector in the upper portion of the condensing zone. The partial condenser was 5.08 centimeters in outside diameter and about 62.5 centimeters in length. The feed stream inlet was located on the side of the partial condenser 7.62 centimeters from the bottom. The bottom of the condensing coil was about 37.1 centimeters above the bottom of the partial condenser. An inlet and an outlet for acetone coolant circulating through the condensing coil were located on the side of the partial condenser near the top. An overhead vapor outlet from the condensing zone was located at the top of the partial condenser. The overhead vapor outlet was sequentially connected to a first scrubbing train, a first gas meter, and a first collection bag of 250 liter capacity. The first scrubbing train consisted of a polyethylene surge vessel containing some water followed by two polyethylene water scrubbers. A condensate outlet was located at the bottom of the partial condenser. The condensate outlet was connected to the longer leg of jacketed 6.35 millimeter stainless steel tubing which was in the shape of a "J". The length of the longer leg was about 116 centimeters while that of the shorter leg was about 47 centimeters. The jacket was 12.7 millimeter stainless steel tubing which was silver-soldered at the ends to the 6.35 millimeter tubing. An inlet and an outlet near opposite ends of the jacket permitted acetone coolant to be circulated through the jacket countercurrently to the flow of condensate in the 6.35 millimeter tubing. Upon leaving the jacketed region, the 6.35 millimeter tubing was connected to one branch of a stainless steel tee. The leg of the tee was connected through a rotameter and valve to a source of nitrogen gas. The other branch of the tee was connected sequentially to a second scrubbing train, a second gas meter, and a second collection bag of 250 liter capacity. The second scrubbing train consisted of a polyethylene surge vessel containing some water followed by two polyethylene water scrubbers. The various parts of the apparatus up to the scrubbing trains were connected as described above using 6.35 millimeter stainless steel tubing and stainless steel fittings. Thereafter polyethylene tubing was used. A small centrifugal pump circulated acetone coolant through the condensing coil of the partial condenser and a copper cooling coil which was immersed in an acetone-solid carbon dioxide bath. Similarly, another small centrifugal pump circulated acetone coolant through the jacket and another copper cooling coil immersed in another acetone-solid carbon dioxide bath. Thermocouples were located at the coolant inlets, at the coolant outlet from the condensing coil, at the bottom of the condensing coil, in the condensing zone at about the level of the feed stream inlet, at the overhead vapor outlet, and on the jacket. The condenser and feed section had a combined volume of 685 milliliters.

The system was operated at about ambient atmospheric pressure. Before beginning a run, the cylinders were weighed, the apparatus was flushed with air or nitrogen, the collection bags were collapsed using a vacuum pump, and acetone coolant was circulated through both cooling loops which were controlled separately. After the partial condenser and the jacketed tubing had been precooled, a calibrated flow of nitrogen gas was established before the second train of water scrubbers to keep a positive flow on the second train of water scrubbers at all times during a run. A run was begun by starting the flow of hydrogen fluoride. In the case of Run 1, when the bend in the jacketed tubing was sufficiently filled with liquid hydrogen fluoride as would permit it to act as a liquid seal, the flows of 1,1,1-trifluoroethane and 1,1-difluoroethene were begun. In the case of Run 2, when the liquid hydrogen fluoride seal was established, the flow of 1,1,1-trifluoroethane was begun. This was continued a few minutes to establish a 1,1,1-trifluoroethane reflux in the partial condenser, after which the flow of 1,1-difluoroethene was begun. In either case, the flows of the three feed stream components were held as nearly constant as possible for the remainder of the run. At the end of a run, the cylinders were reweighed and each of the collection bags was sampled. The concentrations of 1,1,1-trifluoroethane, 1,1-difluoroethene, and air in the samples were determined by gas chromatography. The chromatogram of the samples from the second collection bag showed a small peak having the retention time of 1,1-difluoroethene and the corresponding amounts of 1,1-difluoroethene in the second collection bag were included in the various calculations. However, in view of the substantial residence time of condensate from the condensate outlet of the partial condenser to the second scrubbing train, it is believed unlikely that such 1,1-difluoroethene would have survived in the condensate. It is also believed that this 1,1-difluoroethene was probably introduced to the second collection bag during the initial flushing of the system with air or nitrogen, or by diffusion from the first collection bag since both bags were in physical contact during a run. The gas analyses were normalized to exclude components other than 1,1,1-trifluoroethane and 1,1-difluoroethene. The water from the surge vessel and two water scrubbers of each scrubbing train were combined, weighed, and sampled. The samples were titrated with standard aqueous sodium hydroxide to ascertain the hydrogen fluoride concentrations. Molar amounts of components were calculated from the observed data using molecular weights rounded to the nearest integer. Component accountabilities and reversions of 1,1-difluoroethene based on the appearance of 1,1,1-trifluoroethane, the disappearance of 1,1-difluoroethene, and the disappearance of hydrogen fluoride were separately calculated. In view of the nature of the apparatus, hydrogen fluoride was removed from the overhead vapor soon after the overhead vapor was removed from the partial condenser and the condensing zone. In a commercial plant, however, such hydrogen fluoride would probably not be removed but would be potentially available downstream from the partial condenser for reaction with 1,1-difluoroethene. The 1,1-difluoroethene observed in the second collection bag would also be potentially available for later reaction with hydrogen fluoride. Therefore, the potential total reversion was calculated using the equation:

$$PTR = \frac{(HF)_o + (DFE)_b + (DFE)_i - (DFE)_r}{(DFE)_i} \times 100$$

where:
PTR = Potential total reversion of 1,1-difluoroethene, percent;
$(HF)_o$ = Moles of hydrogen fluoride in the overhead;
$(DFE)_b$ = Moles of 1,1-difluoroethene in the second collection bag;
$(DFE)_i$ = Moles of 1,1-difluoroethene introduced; and
$(DFE)_r$ = Moles of 1,1-difluoroethene recovered.

The conditions and results are shown in the Table. Approximately the first 15 minutes of the run time of each run was made without organic feed to collect liquid hydrogen fluoride in the bend in the jacketed tubing.

In order to run a blank, the apparatus was temporarily modified by connecting the outlet from the manifold to the inlet of the first gas meter, thereby bypassing the partial condenser and the first scrubbing train. The blank was run by introducing only 1,1,1-trifluoroethane and 1,1-difluoroethene from weighed cylinders to the manifold. The resulting gas mixture was then passed through the first gas meter and into the first collection bag. Upon completion of the run, the cylinders were reweighed, the first collection bag was sampled, and the sample was analyzed by gas chromatography. The molar amounts of components and component accountabilities were calculated as before. The conditions and results are also shown in the Table.

The following abbreviations are used in the Table:
TFE = 1,1,1-Trifluoroethane
DFE = 1,1-Difluoroethene
HF = Hydrogen Fluoride

TABLE

| | Run 1 | Run 2 | Blank |
|---|---|---|---|
| Run Length, minutes | 150 | 130 | — |
| Average Temperatures, °C. | | | |
| Coolant In | −65 | −70 | — |
| Condensing Zone | −32 | −50 | — |
| Vapor Outlet | −26 | −32 | — |
| Jacket | −22 | −28 | — |
| Reactants Introduced, moles | | | |
| TFE | 2.786 | 2.762 | 1.214 |
| DFE | 2.938 | 2.703 | 1.593 |
| HF | 3.350 | 3.800 | 0.000 |
| Normalized Gas Analysis, mole percent | | | |
| First Collection Bag | | | |
| TFE | 43.28 | 26.99 | 46.49 |
| DFE | 56.72 | 73.01 | 53.51 |
| Second Collection Bag | | | |
| TFE | 98.21 | 98.26 | — |
| DFE | 1.79 | 1.74 | — |
| Overhead Products Recovered, moles | | | |
| TFE | 2.244 | 0.947 | 1.303 |
| DFE | 2.941 | 2.562 | 1.499 |
| HF | 0.213 | 0.072 | 0.000 |
| Bottoms Products Recovered, moles | | | |
| TFE | 0.466 | 1.541 | — |
| DFE | 0.008 | 0.027 | — |
| HF | 3.071 | 3.614 | — |
| Total Products Recovered, moles | | | |
| TFE | 2.710 | 2.488 | 1.303 |
| DFE | 2.949 | 2.589 | 1.499 |
| HF | 3.284 | 3.686 | 0.000 |
| Reversion of DFE, percent | | | |
| Based on TFE | −2.7 | −9.9 | 7.3 |
| Based on DFE | −0.4 | 4.2 | 5.9 |
| Based on HF | 2.0 | 3.0 | — |
| Potential Total Reversion of DFE, percent | 7.1 | 7.9 | 5.9 |
| Accountabilities, percent | | | |
| TFE | 97.3 | 90.1 | 107.3 |
| DFE | 100.4 | 95.8 | 94.1 |
| HF | 98.0 | 97.0 | — |

The data of Runs 1 and 2 show that within the accuracies of the measurements little or no reversion occurred, which is surprising. These data also show potential total reversions of 1,1-difluoroethene of less than 8 percent which is within acceptable and desirable limits. The data further show that lower operating temperatures favor less hydrogen fluoride in the overhead vapor.

The Blank involved feeding 1,1,1-trifluoroethane and 1,1-difluoroethene without any hydrogen fluoride and measuring what was recovered using the normal analytical and computational procedures that were used on Runs 1 and 2. The accountabilities indicate that 1,1,1-trifluoroethane is about 7 percent long and 1,1-difluoroethene is about 6 percent short. The workup of the data of Runs 1 and 2 does not take into account that there may be response factors which could be used in the gas-liquid chromatographic method to remove these recovery differences. The Blank was not repeated enough times to have any more statistical significance than the other data collected, so these data were not used to adjust the data of Runs 1 and 2. If the Blank data is significant statistically, there is even less reversion than is shown in Runs 1 and 2 and the true reversion may be almost none within increased accuracies of measurement.

Although the present invention has been described with reference to specific details of certain embodiments thereof, it is not intended that such details should be regarded as limitations upon the scope of the invention except insofar as they are included in the accompanying claims.

We claim:
1. A process comprising:
  (a) introducing a gaseous feed stream comprising hydrogen fluoride and 1,1-difluoroethene to a condensing zone,

(b) contacting said feed stream in said condensing zone with liquid organic barrier material to partially condense said feed stream and produce a gaseous phase comprising most of the 1,1-difluoroethene originally present in said feed stream and a liquid condensate comprising most of the hydrogen fluoride originally present in said feed stream, and (c) removing said gaseous phase and said liquid condensate from said condensing zone as separate streams, wherein less than about 50 percent of the 1,1-difluoroethene originally present in said feed stream reacts with hydrogen fluoride to form 1,1,1-trifluorethane during the partial condensation and the removal of said separate streams from said condensing zone.

2. The process of claim 1 wherein less than about 25 percent of the 1,1-difluoroethene originally present in said feed stream reacts with hydrogen fluoride to form 1,1,1-trifluoroethane during the partial condensation and the removal of said separate streams from said condensing zone.

3. The process of claim 1 wherein less than about 10 percent of the 1,1-difluoroethene originally present in said feed stream reacts with hydrogen fluoride to form 1,1,1-trifluoroethane during the partial condensation and the removal of said separate streams from said condensing zone.

4. The process of claim 1 wherein less than about 5 percent of the 1,1-difluoroethene originally present in said feed stream reacts with hydrogen fluoride to form 1,1,1-trifluoroethane during the partial condensation and the removal of said separate streams from said condensing zone.

5. The process of claim 1 wherein said gaseous phase which is removed from said condensing zone comprises at least about 50 percent of the 1,1-difluoroethene originally present in said feed stream and less than about 10 percent of the hydrogen fluoride originally present in said feed stream.

6. The process of claim 1 where said liquid condensate which is removed from said condensing zone comprises at least about 65 percent of the hydrogen fluoride originally present in said feed stream and less than about 1 percent of the 1,1-difluoroethene originally present in said feed stream.

7. The process of claim 1 wherein said liquid organic barrier material comprises 1,1,1-trifluoroethane.

8. A process comprising:

(a) introducing a gaseous feed stream comprising 1,1-difluoroethene and hydrogen fluoride to a condensing zone, (b) contacting said feed stream in said condensing zone with liquid organic barrier material to partially condense said feed stream and produce a gaseous phase comprising most of the 1,1-difluoroethene originally present in said feed stream and a liquid condensate comprising two liquid phases, one of said liquid phases comprising most of the hydrogen fluoride originally present in said feed stream and the other of said liquid phases comprising liquid organic barrier material, and (c) removing said gaseous phase and said liquid condensate from said condensing zone as separate streams, wherein less than about 50 percent of the 1,1-difluoroethene originally present in said feed stream reacts with hydrogen fluoride to form 1,1,1-trifluoroethane during the partial condensation and the removal of said separate streams from said condensing zone.

9. The process of claim 8 wherein less than about 25 percent of the 1,1-difluoroethene originally present in said feed stream reacts with hydrogen fluoride to form 1,1,1-trifluoroethane during the partial condensation and the removal of said separate streams from said condensing zone.

10. The process of claim 8 wherein less than about 10 percent of the 1,1-difluoroethene originally present in said feed stream reacts with hydrogen fluoride to form 1,1,1-trifluoroethane during the partial condensation and the removal of said separate streams from said condensing zone.

11. The process of claim 8 wherein less than about 5 percent of the 1,1-difluoroethene originally present in said feed stream reacts with hydrogen fluoride to form 1,1,1-trifluoroethane during the partial condensation and the removal of said separate streams from said condensing zone.

12. The process of claim 8 wherein said gaseous phase which is removed from said condensing zone comprises at least about 50 percent of the 1,1-difluoroethene originally present in said feed stream and less than about 10 percent of the hydrogen fluoride originally present in said feed stream.

13. The process of claim 8 wherein said liquid condensate which is removed from said condensing zone comprises at least about 65 percent of the hydrogen fluoride originally present in said feed stream and less than about 1 percent of the 1,1-difluoroethene originally present in said feed stream.

14. The process of claim 8 wherein said liquid organic barrier material comprises 1,1,1-trifluoroethane.

* * * * *